United States Patent [19]

Ingalz et al.

[11] Patent Number: 4,886,066
[45] Date of Patent: Dec. 12, 1989

[54] TONOMETER HAVING ACOUSTIC COUPLING DETECTION

[75] Inventors: Thomas J. Ingalz, San Jose; Jerry B. Gin, Sunnyvale, both of Calif.; Vernon G. Wong, Rockville, Md.

[73] Assignee: See Care Corporation, Sunnyvale, Calif.

[21] Appl. No.: 244,144

[22] Filed: Sep. 13, 1988

[51] Int. Cl.[4] .............................................. A61B 3/16
[52] U.S. Cl. .................................................. 128/645
[58] Field of Search ............... 128/645, 646, 647, 649, 128/653, 660.02, 660.06, 661.07, 748, 774, 782; 73/574, 589, 605, 627

[56] References Cited

U.S. PATENT DOCUMENTS

| | | | |
|---|---|---|---|
| 3,049,001 | 8/1962 | MacKay et al. | 128/645 |
| 3,338,089 | 8/1967 | Cuombs, Jr. et al. | 128/652 |
| 3,443,421 | 3/1969 | Poswer et al. | 128/652 |
| 3,511,085 | 5/1970 | Dosner et al. | 128/652 |
| 3,557,611 | 1/1971 | Adisg | 128/645 |
| 3,680,028 | 7/1972 | Black | 128/645 |
| 3,948,248 | 5/1976 | Zockerman et al. | 128/662.01 |
| 4,621,644 | 11/1986 | Filers | 128/652 |

FOREIGN PATENT DOCUMENTS

| | | | |
|---|---|---|---|
| 146907 | 3/1961 | U.S.S.R. | 128/652 |
| 1138110 | 2/1985 | U.S.S.R. | 128/652 |

Primary Examiner—William E. Kamm
Attorney, Agent, or Firm—Thomas Schneck

[57] ABSTRACT

A tonometer for measuring the intraocular pressure of an eye featuring an acoustic signaling system for determining the beginning of a pressure measurement. The acoustic system includes a consumable cap having a pair of annular raised surface portions spaced by a recessed area. The raised surface portions provide an eye-engaging surface at the face of the tonometer. A pressure transmitting plunger concentrically suspended between the raised surface portions by a plurality of spider arms combines with the eye-engaging surface to provide a contour which complements a shape of an eye. The recessed area is open along the eye-engaging surface, yet defines a generally enclosed volume when full tonometer-to-eye contact is made. Spaced apart inlet and outlet apertures within the recessed area permit channeling of an acoustic signal to and from the recessed area. Prior to proper coupling of the tonometer to an eye, a substantial amount of the energy of the acoustic signal is lost to free air. However, upon achieving full tonometer-to-eye contact the energy is captured within the recessed ara and channeled to an acoustic receiver when the plunger contacts the eye, constricting the inlet-to-outlet acoustic wave path. Characteristic change of the received signal is marked by a hold signal triggered to initiate an intraocular pressure measurement. Proper coupling may be detected by either monitoring the phase or the change in amplitude at the acoustic wave receiver. Intraocular pressure is measured by means of the plunger which is operatively coupled to a force transducer.

20 Claims, 3 Drawing Sheets

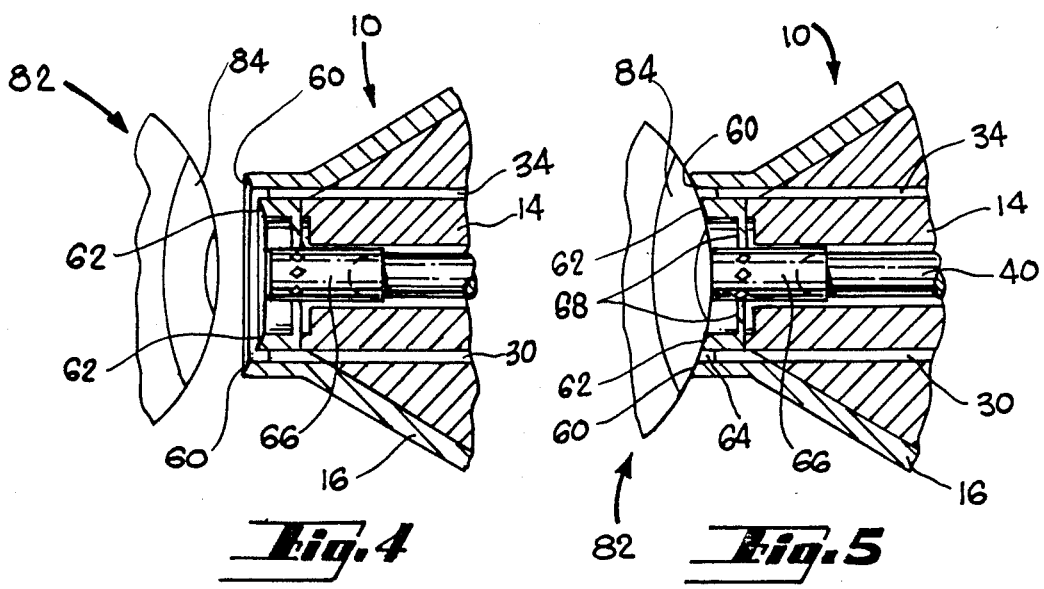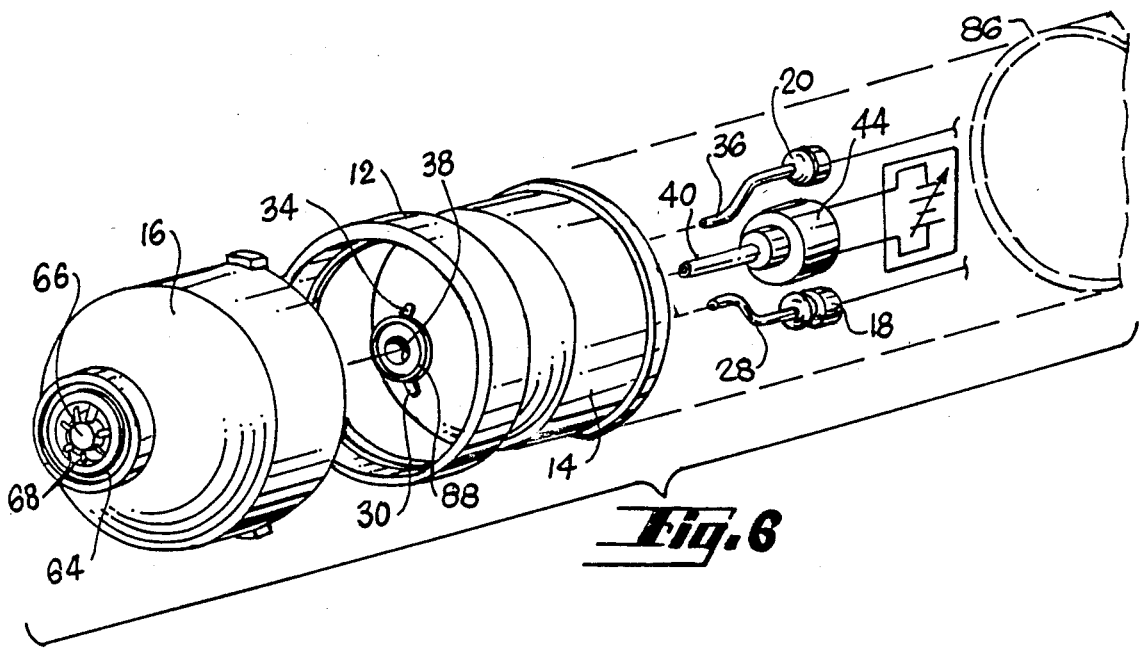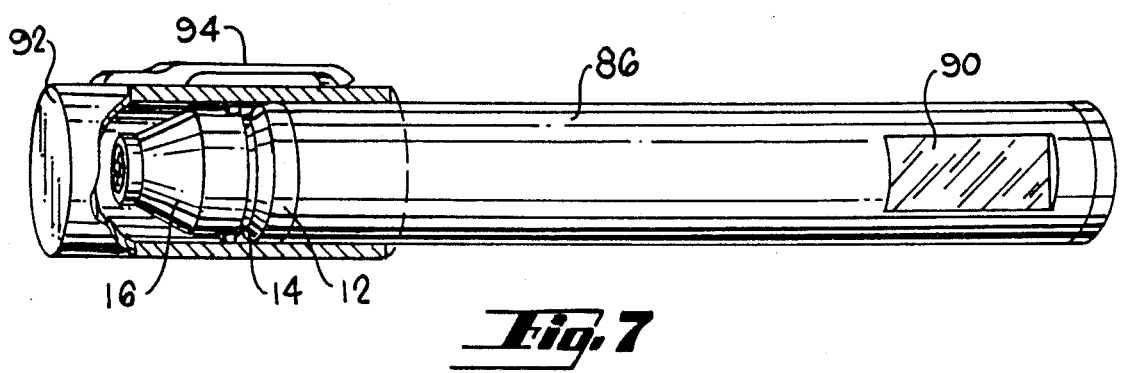

TONOMETER HAVING ACOUSTIC COUPLING DETECTION

TECHNICAL FIELD

The invention relates generally to the field of tonometry and particularly to apparatus for measuring the intraocular pressure of an eye.

BACKGROUND ART

Glaucoma is a disease of the eye characterized by increased pressure within the eyeball. If left untreated, glaucoma leads to a gradual impairment of sight which may result in blindness. The disease is prevalent among the population over 40 years of age, but develops slowly and often remains asymptomatic until well advanced.

Tonometry is the noninvasive measurement of intraocular pressure of the eye. Use of a tonometer for measurement of the intraocullar pressure is an important tool for the detection and treatment of glaucoma and other eye disorders. Typically, a tonometer includes a ring-and-plunger arrangement which is brought into contact with the eye. The plunger is mounted to permit movement relative to the ring. The force on the plunger with respect to the ring is then directly translated into intraocular pressure measurements.

To avoid pressure understatements or overstatements, it is imperative that the axis of the ring-and-plunger arrangement contact the eye perpendicular to the center line of the eye. The requirement of perpendicularity may be satisfied by use of an examination chair tonometer unit, but the cost of such units limits their effective availability. Methods of detecting perpendicularity of a tonometer with respect to an eye are utilized to safeguard against understatements of intraocular pressure. For example, U.S. Pat. No. 3,338,089 to Coombs, Jr. et al. utilizes photosensing for imaging of the area of contact with the eye under test, while U.S. Pat. No. 4,621,644 to Eilers teaches developing an area-proportional signal responsive to the area of contact.

Another source of error in intraocular pressure measurements stems from the variance of positioning force of the tonometer on the eye. With skilled handling this bias may be moderated, but an overstatement of 2 to 15 mm Hg may still occur depending upon the tonometer used. This is a significant problem since the clinical range of intraocular pressure for the population is between 8 to 28 mm Hg. To combat this problem U.S. Pat. No. 3,948,248 to Zuckerman et al. teaches using ultrasonic energy to observe ocular pulses. However, the ultrasonic measurement requires highly specialized equipment and a trained operator.

Other factors which must be considered in designing a tonometer that contacts an eye include the potential for cross contamination of patients. The bodily fluids of an eye may contaminate the eye of a subsequent user if a tonometer is not adequately sterilized after each use.

Conventional noninvasive measuring of intraoculator pressure is performed by contacting the cornea. Because of the sensitivity of the cornea, an anesthetic is applied injury is greater about the cornea than the potential of injury involved with contacting the sclera area of the eye. Measurements of intraocular pressure at the sclera area of the eye would eliminate the need of anesthetic administration and would open the field of tonometry to general practitioners and even to home use. But low-cost tonometers have as of yet been unsuccessful in gathering accurate intraocular pressure measurements at the sclera because of the tough shell of the sclera.

It is an object of the present invention to provide a low-cost tonometer which is accurate at the cornea and sclera, yet which does not require a highly trained operator.

DISCLOSURE OF THE INVENTION

The above object has been met by the discovery that tonometer accuracy may be increased by accurately determining the moment of contact between a pressure member and the eye. If the moment of contact is not accurately determined, good pressure measurements cannot be made. In the present invention, the instantaneous coupling between a tonometer pressure member and the eye is detected using acoustic waves. The generated acoustic waves are channeled to a first area of an eye-contacting cap part of a pressure transmitting tonometer assembly, and are received at a second area of the cap. The characteristics of the acoustic waves at the second area are monitored to determine when the coupling of the cap to an eye is maximized.

The face of the cap has first and second eye-seating raised surface segments spaced apart by an annular recessed surface segment. An acoustic wave signal-transmitting channel has an outlet within the recessed surface segment, while a signal-receiving channel has an inlet within the recessed surface segment at an area spaced apart from the signal-transmitting channel. A plunger is axially suspended at the face of the cap for movement relative to the cap, whereby such movement transmits pressure from a pressure source.

Acoustic waves passing through the signal-transmitting channel are, under normal circumstances, lost to the atmosphere surrounding the cap. However, when full cap-to-eye contact is made, the eye along with the annular recessed surface segment define an enclosed volume. This enclosed volume captures the acoustic waves for propagation to the inlet of the signal-receiving channel. Consequently, proper coupling of the eye-seating raised surface segments to an eye undergoing testing causes an increase in amplitude within the signal-receiving channel. Moreover, the phase of the received signal will lag the phase of the transmitted signal. The characteristics of the received signal, therefore, may be monitored to detect proper coupling. At that time, a hold signal is generated to mark the moment of contact between the pressure member and the eye.

The pressure transmitting plunger is suspended at the cap by a plurality of spider arms. During full cap-to-eye contact one end of the plunger engages the eye. The opposite end of the plunger is operatively coupled to a pressure sensing device. Upon receiving a hold signal, the pressure sensing device is polled and the resulting intraocular pressure measurement is displayed on a liquid crystal display of the tonometer.

An advantage of the present invention is that proper coupling of the tonometer to an eye under test is insured. The coupling need only be momentary since the intraocular pressure sensing device is polled as soon as coupling is maximized. Further depression of the eye by the tonometer after the hold event will not have a bearing on the resulting displayed intraocular pressure measurement value.

Another advantage is that the cap-and-plunger arrangement is slidably fit to he nose of the tonometer. The cap is made of an injection molded plastic Thus, the cap is consumable article which may be discarded after use. Any patient cross contamination risk is therefore removed. The cap and plunger define a concave face which complements the average sclera curvature. It has been discovered that the cap and acoustic contact detection assembly provide low-cost, simple, reliable measurements even when the tonometer is coupled at the sclera area of an eye.

BRIEF DESCRIPTION OF THE DRAWINGS

FIGS. 4 and 5 are operational side sectional views of the tonometer of FIG. 1.

FIG. 6 is an exploded view of the tonometer of FIG. 1.

FIG. 7 is a perspective view of a fully-constructed tonometer of FIG. 6.

BEST MODE FOR CARRYING OUT THE INVENTION

Figure 1:
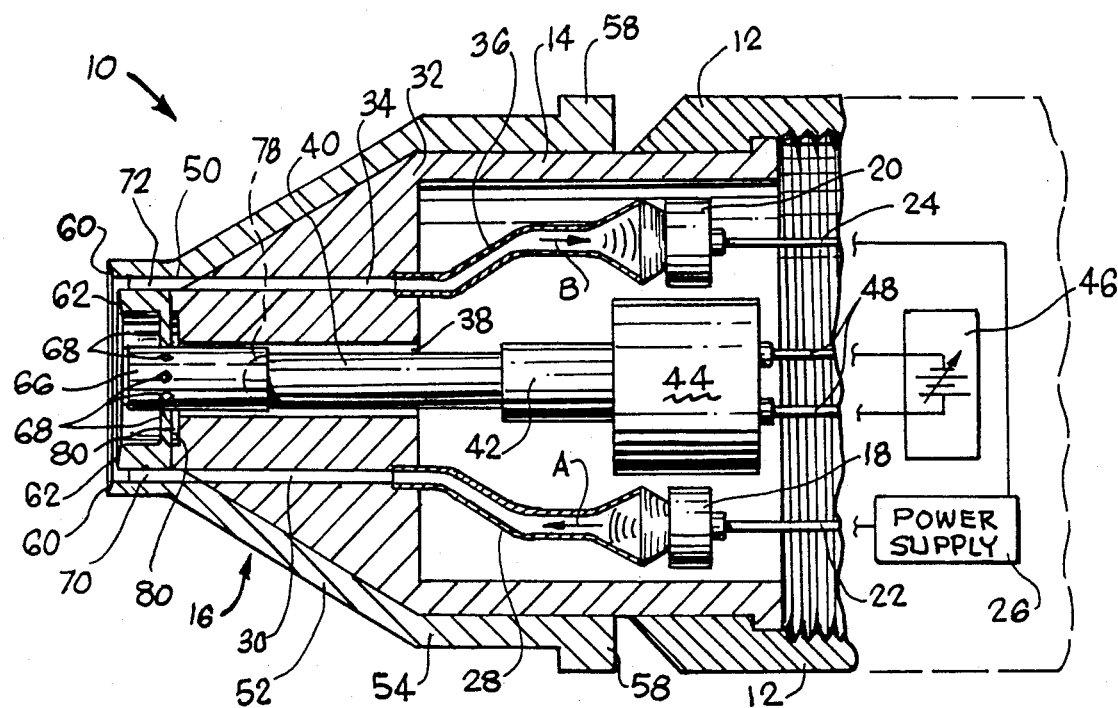
FIG. 1 is a fragmentary side sectional view of a tonometer in accord with the present invention.

With reference to FIG. 1, the forward portion of a tonometer 10 includes a housing 12 having a nose portion 14. A cap 16 is slidably received onto the nose portion 14 for frictional engagement with the nose portion.

The nose portion 14 houses an acoustic transmitter and an acoustic receiver 20. Conductive wires 22 and 24 provide attachment to a power supply 26 for driving the acoustic transmitter and receiver 18 and 20. The acoustic transmitter may be a conventional miniature speaker, while the receiver is a miniature audio microphone. The acoustic transmitter 18 generates acoustic waves through a conduit 28, as shown by arrow A. The frequency of the waves is not important, but an audio frequency is convenient and preferred, nominally 3.0 KHz. The end of the conduit 28 opposite the transmitter acoustically communicates with a transmitting channel 30 through a tapering segment 32 of the nose portion. The tapering segment 32 also includes a receiving channel 34 in communication with a second conduit 36. Vibrations within the receiving channel 34 will be propagated through the second conduit 36 to the acoustic receiver 20, as shown by arrow B. The conduits 28 and 36 are preferably made of metal, but in any case should not impede the passage of acoustic signals through the conduits.

A central bore 38 through the tapering segment 32 of the nose portion 14 receives a piston 40. The piston is enlarged at an inner end 42 and is connected to a silicon piezo resistive force transducer 44. The transducer 44 is of the type commonly used in the art, having a Wheatstone bridge configuration. The transducer is a strain gauge which measures pressure exerted onto the piston 40 and is represented by the symbol 46. Conductive wires 48 permit communication between the transducer 44 and control circuitry.

Figure 2:
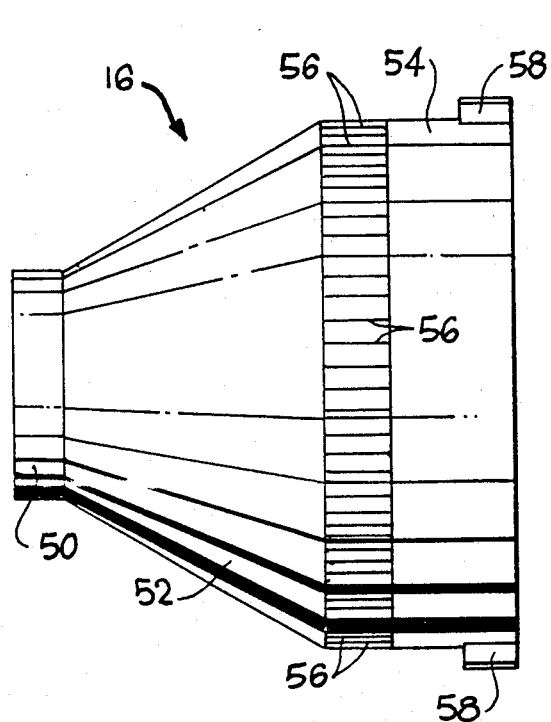
FIG. 2 is a side view of the cap of FIG. 1.
Figure 3:
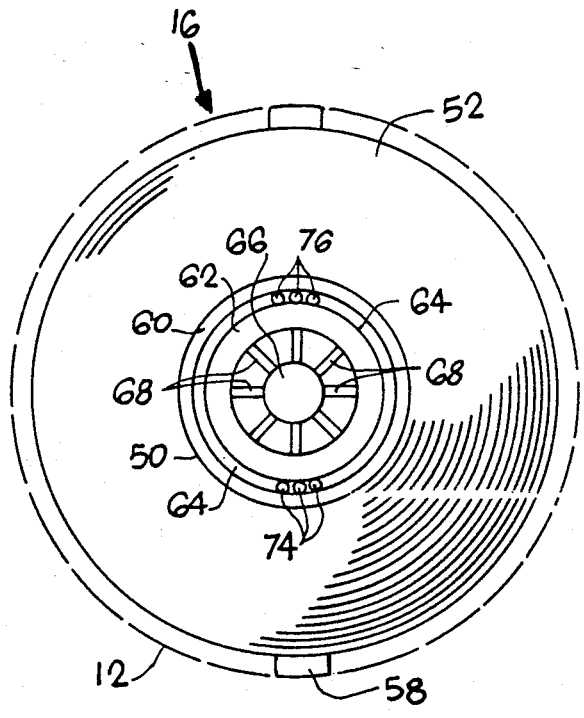
FIG. 3 is a front view of the cap of FIG. 2.

Referring now to FIGS. 1–3, the cap 16 is a single-use consumable unit. The consumable cap includes a cylindrical face portion 50, a frustroconical portion 52 and an annular rear portion 54. The frustroconical portion 52 and the annular rear portion 54 each have an inside diameter slightly larger than the outside diameter of the nose portion 14 of housing 12. Thus, the seating of the cap 16 onto the tonometer 10 is a frictional engagement.

The annular rear portion 54 includes a plurality of spline-like projections 56 to facilitate gripping and includes a pair of tabs 58.

The consumable cap 16 is made of an injection molded plastic. Prior to use the consumable cap is slidably fit onto the nose portion 14 of a tonometer 10. Conventional tonometers must be sterilized between uses in order to prevent cross contamination of patients. Utilization of a consumable cap 16, however, removes the risk of cross contamination. Preferably, the consumable cap is damaged in some manner upon removal from the nose portion 14 of the tonometer to ensure against subsequent use.

The face portion 50 of the consumable cap 16 includes a first annular raised surface 60 and a second annular raised surface 62. The raised surfaces 60 and 62 combine to form an eye-engaging surface having a contour to complement the curvature of an eye. The raised surfaces are spaced apart by a recessed area 64, as shown in FIG. 3. A plunger 66 is coaxially suspended within the raised surfaces 60 and 66 by a plurality of spider arms 68. Preferably, the spider arms are eight in number and are sufficiently flexible to permit movement of the plunger 66 relative to the consumable cap 16. The spider arms 68 position the plunger for contact with an eye to be tested, and the end of the plunger has a contour which further complements the contour of the eye.

Referring still to FIGS. 1 and 3, the consumable cap 16 has a first channel 70 which further defines the transmitting channel 30 of the tonometer 10. A second channel 72 through the consumable cap further defines the receiving channel 34. At the face of the consumable cap three outlet apertures 74 within the recessed area 64 permit communication of the acoustic transmitter 18 with the outside atmosphere. In like manner, three inlet apertures 76 within the recessed area permit communication between the outside atmosphere and the acoustic receiver 20.

The interior end of the plunger 66 has a detent 78 to receive the arcuate end of the piston 40. Thus, movement of the plunger is registered at the piezo resistive pressure transducer 44. A cavity 80 immediately rearward the spider arms 68 allows the spider arms to flex when pressure is exerted onto the plunger 66.

In operation, FIG. 4 shows a tonometer 10 aligned for contact with an eye 82. An acoustic signal is propagated from the transmitting channel 30. For example, a signal of 3 KHz may be transmitted, but this frequency is not critical. With the tonometer spaced apart from the eye 82 acoustic waves enter the ambient atmosphere. A relatively small portion of the waves will reflect from the eye to the receiving channel 34. An even smaller portion will be picked up at the receiving channel via conduction through the nose portion 14 of the tonometer or will be detected through electromagnetic coupling.

Referring now to FIG. 5, the tonometer 10 is progressed forwardly until the annular raised surfaces 60 and 62 and the plunger 66 all contact the cornea 84 of the eye. Although the raised surfaces 60 and 62 and the plunger 66 form a concave eye-contacting surface, the tonometer 10 is an applanation tonometer which flattens a portion of the cornea 84. Contact of the plunger against the eye flexes the spider arms 68 to a degree dependent upon the intraocular pressure of the eye 82. Movement of the plunger 66 relative to the cap 16 is translated to the piston 40, permitting a measurement of intraocular pressure by the piezo resistive force transducer.

A precise measurement of intraocular pressure is possible only when a tonometer is correctly seated against an eye 82. Typically, tonometers require use by a highly trained operator who is able to achieve perpendicularity of the tonometer axis with respect to a vertical center line of an eye. The present tonometer 10, however, insures that a reading of intraocular pressure is taken only at the moment at which perpendicularity has been achieved. As noted with reference to FIG. 4, when the tonometer is removed from an eye 82 much of the energy of the acoustic waves generated through the transmitting channel 30 is lost to free air. In contrast, with the tonometer seated against the eye in a perpendicular manner, as shown in FIG. 5, the energy is captured within the recessed area 64 between raised surfaces 60 and 62. The energy captured within the annular recessed area 64 will travel from the outlets of the transmitting channel 30 to the inlets of the receiving channel 34. Correct seating of an eye against the tonometer 10 may therefore be detected by a dramatic increase in volume through the receiving channel.

Alternatively, correct seating may be detected by monitoring of the phase relationship between the transmitted acoustic waves and the energy through receiving channel 34. As the acoustic waves progress through the annular recessed area 64 to the receiving channel 34 and into the acoustic receiver, a phase lag will occur. For example, the signal at the acoustic receiver may lag the signal at the acoustic transmitter by 90 degrees to 100 degrees. This phase change detection method is preferred. In actuality, a phase change of 90 degrees is detected whenever there is a lag that is 90 degrees plus a multiple of 360 degrees. Thus, the actual phase change is 360 n+90°, with n equal to the number of cycles which the received signal lags the transmitted signal. The exact phase change depends upon the structure of the tonometer 10. This phase change value (i.e., delta value) is not critical to proper operation of the tonometer.

When the desired phase shift has been registered, a hold signal is generated. The circuitry of the tonometer will be outlined more fully below, but generation of the hold signal causes an intraocular pressure measurement to be captured and read out onto a display. Once the intraocular pressure measurement has been captured, further movement of the tonometer has no consequence. That is, further depression of the eye by the tonometer or any misalignment of the tonometer-to-eye positional relationship will not affect the displayed measurement. The result is that the tonometer is less susceptible to operator error, permitting use by general practice physicians and individual glaucoma patients who can adjust medication dosages according to changes in intraocular pressure.

While FIGS. 4 and 5 show the tonometer 10 as being coupled to a cornea 84, it has been discovered that the tonometer may be used in taking measurements on the scleroic wall of the eye. Scleroic wall measurements present less risk of eye injury. The tough shell of the sclera has in the past made such measurements less reliable, but the concave eye-contacting surface and acoustic contact detection of the present invention provide reliable measurements.

Referring now to FIG. 6, the exploded view shows a consumable cap 16 which slidably fits on a nose portion 14. The nose portion is attached to the remainder of the housing 86, shown in phantom, by a housing annulus 12. The housing annulus is internally threaded and is secured to the external threads of the housing. The conduit 28 of the acoustic transmitter 18 fits within the transmitting channel 30 of the nose portion. Likewise, the second conduit 36 of the acoustic receiver 20 is snug fit within the receiving channel 34 of the nose portion. The transmitting and receiving channels 30 and 32 communicate with the surrounding atmosphere via apertures within the recessed area 64 at the face of the consumable cap 16.

The piston 40 of the piezo resistive force transducer 44 extends through the central bore 38 of the nose portion 14. The piston 40 contacts the rearward end of the plunger 66. A ring-like projection 88 about the central bore 38 of the nose portion defines the cavity 80 shown in FIG. 1 for flexing of the spider arms 68.

FIG. 7 shows the housing 86 as being a pen-type construction. The consumable cap 16 is slidably fit on the nose portion 14 which is threadably tightened to the housing 86 by the housing annulus 12. The housing has a liquid crystal display 90 and a removable cap 92 with a grasping clip 94. The pen style is shown as one embodiment of the present invention and is not critical.

Figure 8:
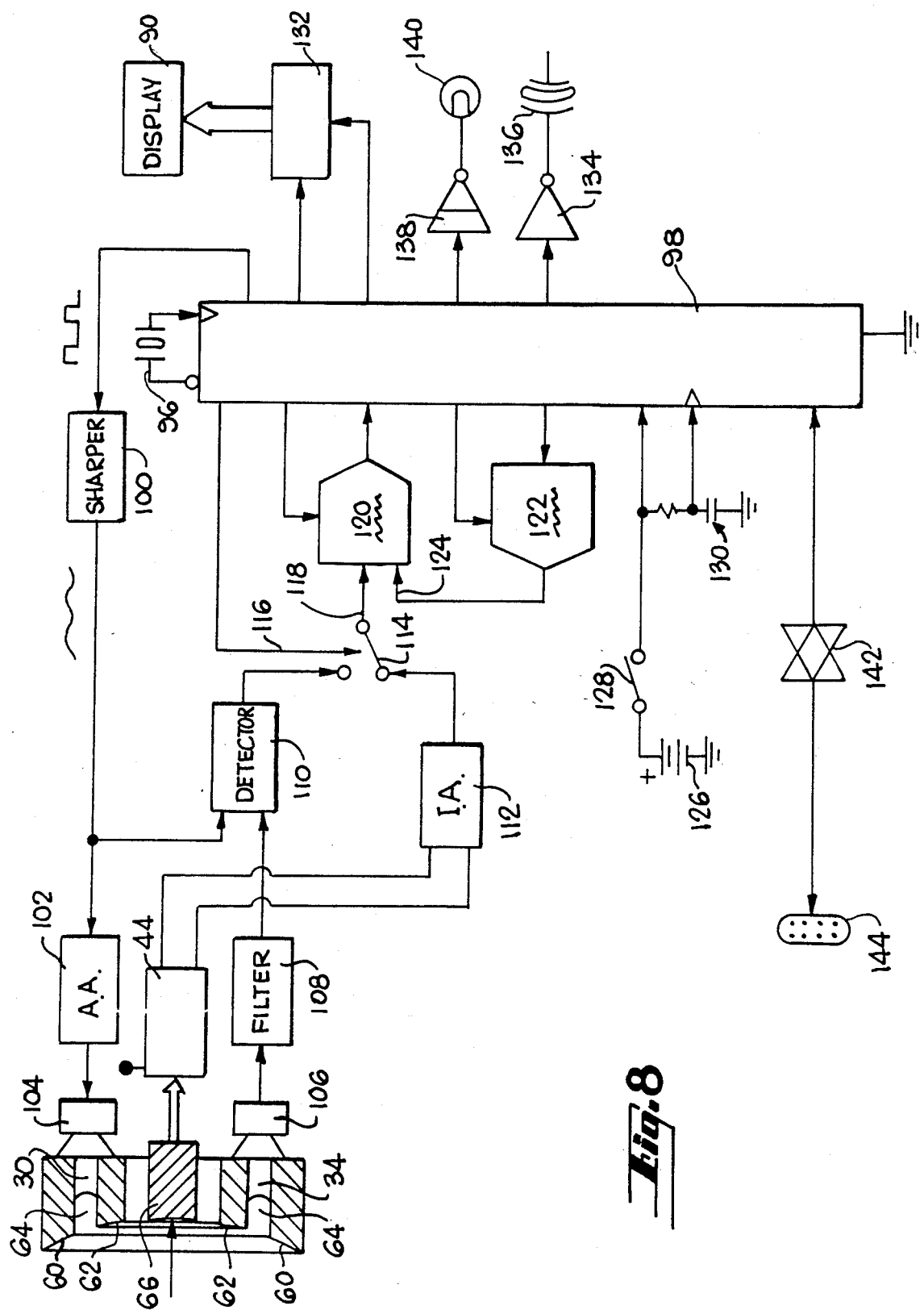
FIG. 8 is a block diagram of the tonometer of FIG. 7.

FIG. 8 is exemplary of the tonometer circuitry. A clock oscillator 96 is linked to a microcontroller 98 which produces a square wave at a sine wave shaper 100. The square wave has a frequency of 3 KHz but, again, the frequency is not critical. At the sine wave shaper 100 the square wave is converted to a sine wave. The sine wave is then amplified at an audio amplifier 102 and transmitted into a transmitting channel 30 by a speaker 104. Under normal circumstances the audio signal progresses past the annular raised surfaces 60 and 62 shown in FIGS. 1 and 8. As the raised surfaces 60 and 62 along with the plunger 66 are brought into contact with an eye, however, the energy of the audio signal is captured within the recessed area 64 defined by the raised surfaces 60 and 62. Instead of the energy being lost to the surrounding atmosphere, the energy enters the receiving channel 34 to cause vibrations in an audio microphone 106. The electrical signal from the microphone 106 enters a passband active filter 108 which filters out undesired frequencies such as those produced by operator contact with the tonometer.

A phase error detector 110 has the function of comparing the frequency from the passband active filter 108 and the phase of the acoustic waves from the sine wave shaper 100. The reference signal for the phase error detector 110 may come from a direct connection to the sine wave shaper 100 or may come from the almost unavoidable electromagnetic coupling of wiring and power supply lines as well as mechanical coupling of parts. Typically, the phase of acoustic waves from the filter 108 lags the reference signal by 90 degrees to 100 degrees during full tonometer-to-eye contact, but a range of 90 to 100 degrees is not a range that is critical to the present invention.

The plunger 66 is in mechanical communication with the silicon piezo resistive force transducer 44. Displacement of the plunger by intraocular pressure of an eye is detected by the force transducer. Measurements are amplified by in instrumentation amplifier 112 which is linked to one terminal of a CMOS analog switch 114. The switch 114 is operated by the microcontroller 98, as represented by the input switch control line 116. The switch 114 alternatively connects a first input line 118 of an analog-to-digital converter 120 to the instrumentation amplifier 112 or the phase error detector 110.

In initiating the tonometer the first input 118 of the analog-to-digital converter 120 is linked to the instrumentation amplifier 112. Because the plunger 66 is part of a consumable device, compensation must be made for inconsistencies among consumable devices. The injection molding of the devices may be less than perfect and attachment of the consumable device to the tonometer will cause variances in the pressure of the plunger 66 upon the force transducer 44 even before contact is made with an eye. Moreover, as the ambient temperature changes and the material expand, the pressures involved will vary. Therefore, to obtain a precise intraocular pressure measurement any initial pressure upon the transducer 44 must be subtracted from the reading taken at the time of coupling with an eye. The analog-to-digital converter 120 together, with the microcontroller 98 and a digital-to-analog converter 122 cooperate to provide a compensation voltage via a second input 124 of the analog-to-digital converter 120.

In operation, a battery 126 powers the microcontroller 98 upon activation of an on-off switch 128. A reset circuit 130 may be employed to ready the circuitry. Initialization causes the CMOS analog switch 114 to connect the first input 118 of the analog-to-digital converter 120 to the instrumentation amplifier 114. The converters 120 and 122 and the microcontroller 98 provide the compensation voltage to the analog-to-digital converter 120, after which the CMOS analog switch links the first input 118 to the phase error detector 110. The phase error detector monitors the difference in phase at its two inputs and when the phase from the pass band active filter 108 is lagging by 90 degrees to 100 degrees, the tonometer circuitry initiates a hold signal. The hold signal causes the CMOS analog switch 114 to again link the instrumentation amplifier 112 to the first input 118 of the converter 120. An intraocular pressure reading defined by the force of the plunger 66 against the transducer 44 is immediately taken. A precise measurement is obtained by subtraction of the above-defined compensation voltage. An intraocular pressure measurement is amplified by a display driver 132 and read out onto a liquid crystal display 90.

FIG. 8 illustrates a number of optional features. A driver 134 and buzzer 136 may be included to signal an operator that proper tonometer-to-eye coupling has been achieved. A second driver 138 and a fixation lamp 140 are important in taking scleroic wall readings. The fixation lamp provides a point of focus for properly positioning the cornea during coupling of the tonometer to the scleroic wall. Finally, a bi-directional communication line driver 142 is linked to a connector 144 where serial communication with other components is desired.

For purposes of this application, "acoustic" is synonymous with "pressure" so that an acoustic wave is a pressure wave, i.e. a wave not dependent on audible frequencies. Further, while the circuitry of FIG. 8 has been described as having a phase error detector, it is understood that the monitoring of phase may be replaced by circuitry monitoring the change in amplitude as the consumable cap is coupled to an eye to be tested. Related characteristics may also be monitored.

We claim:

1. A tonometer for measuring the intraocular pressure of an eye, comprising,
    a contacting member having an eye-engaging surface, said eye-engaging surface having at least one raised portion and a recessed portion, said recessed portion being open along said raised portion yet defining a generally enclosed volume when said eye-engaging surface is in contact with an eye under test,
    means for generating an acoustic test signal and channeling said test signal to a first sector of said recessed area,
    means for receiving said acoustic test signal at a second sector of said recessed area spaced apart from said first sector,
    means for monitoring characteristics of said acoustic test signal received at said second sector and for detecting a variance when said characteristics satisfy at least one preselected condition, thereby indicating eye contact, and
    means for sensing the pressure exerted by said eye on said contacting member when said eye-engaging surface is indicated to be in contact with said eye.

2. The tonometer of claim 1 further comprising a housing having structure supporting an acoustic wave transmitter and an acoustic wave receiver for generating and receiving of said test signal, said housing having a nose portion, said contacting member having a configuration to be slidably received by said nose portion.

3. The tonometer of claim 1 wherein said housing has dimensions permitting the housing to be hand held.

4. The tonometer of claim 1 wherein said means for sensing the pressure exerted by an eye includes a plunger supported to said contacting member at a plurality of spider arms, said plunger having an axis aligned for perpendicular contact with said eye.

5. The tonometer of claim 1 wherein said recessed area is an annular depression in said eye-engaging surface.

6. The tonometer of claim 1 wherein said means for generating and channeling a test signal to said first sector of the recessed area includes at least one internal wall in said contacting member defining a transmitting channel, said transmitting channel having an outlet at said first sector of the recessed area.

7. The tonometer of claim 1 wherein said means for receiving the test signal at said second sector of said recessed area includes at least one internal wall in said contacting member defining a receiving channel, said receiving channel having an inlet at said second sector of the recessed area.

8. The tonometer of claim 1 wherein said acoustic test signal has a known frequency and said means for monitoring characteristics of said test signal trigger said hold signal in accord with one of the phase of said test signal and the amplitude of said test signal at the second sector of the recessed area.

9. A tonometer of the type having a suspended force-transmitting member having a first end adapted for engagement with an eye to be tested and having a second end operatively attached to a pressure-sensing device, the improvement comprising,
    a cap having an eye-engaging surface, said eye-engaging surface having a first portion of a shape to seat an eye to be tested and having a second portion that is recessed relative to said first portion and said eye, said recessed second portion combining with said eye to form a generally enclosed volume, said cap having at least one transmitting channel and at least one receiving channel having apertures at spaced apart areas of said recessed second portion, means for generating an acoustic test signal in said transmitting channel, means for detecting said acoustic test signal in said receiving channel, and means for comparing the characteristics of said acoustic test signal within said receiving channel relative to the characteristics of said test signal within said transmitting channel.

10. The tonometer of claim 9 wherein said force-transmitting member is a plunger suspended from said cap by a plurality of spider arms, said cap being slidably fit to a tonometer housing.

11. The tonometer of claim 10 wherein said plunger is a cylindrical member and wherein the cap, the plunger and the spider arms are made of an injection molded plastic.

12. The tonometer of claim 9 wherein said eye-engaging surface has an annular configuration and said eye-seating first portion is divided by said recessed second portion, said second portion being annular.

13. The tonometer of claim 9 further comprising a housing having dimensions adapted to be hand held.

14. The tonometer of claim 13 wherein said means for comparing the characteristics of said test signal in said receiving channel includes circuitry monitoring one of the amplitude of the test signal and the phase of the test signal.

15. A tonometer comprising, a tonometer housing having a nose portion, a cap having a shape to slidably receive said nose portion, said cap having a face having first and second eye-seating raised surface segments spaced apart by an annular recessed surface segment, said cap having a signal-transmitting channel having an outlet within said recessed surface segment and said cap having a signal-receiving channel having an inlet within said recessed surface segment spaced apart from said outlet, a plunger suspended at said face of the cap, said plunger mounted for movement relative to said cap and having a first end adapted to contact an eye and having a second end operatively coupled to a pressure-sensing device, a means for conducting an acoustic test signal to said transmitting channel of the cap, and means for monitoring the characteristics of said test signal in said receiving channel.

16. The tonometer of claim 15 wherein said means for monitoring includes circuitry for testing of one of the amplitude and the phase of the signal in said receiving channel.

17. The tonometer of claim 15 further comprising a housing having dimensions adapted to be hand held.

18. The tonometer of claim 15 wherein said first and second eye-seating surface segments form a concave eye-engaging surface.

19. The tonometer of claim 15 wherein said plunger is suspended by spider arms projecting from said cap, said plunger disposed along the axis of said cap.

20. The tonometer of claim 15 wherein said second end of the plunger is in frictional contact with a piston of a strain gauge.

* * * * *